United States Patent
Zhang et al.

(10) Patent No.: US 10,227,603 B2
(45) Date of Patent: Mar. 12, 2019

(54) PLANTS AS FUNCTIONAL MICRORNA AND/OR FUNCTIONAL SIRNA CARRIERS, PREPARATION METHODS AND USES THEREOF

(71) Applicant: MICROMEDMARK BIOTECH CO., LTD., Beijing (CN)

(72) Inventors: Chenyu Zhang, Beijing (CN); Zhi Hong, Beijing (CN); Ke Zeng, Beijing (CN)

(73) Assignee: MICROMEDMARK BIOTECH CO., LTD., Beijing (CN)

(*) Notice: Subject to any disclaimer, the term of this patent is extended or adjusted under 35 U.S.C. 154(b) by 0 days.

(21) Appl. No.: 14/415,401

(22) PCT Filed: May 15, 2013

(86) PCT No.: PCT/CN2013/075642
§ 371 (c)(1),
(2) Date: Jan. 16, 2015

(87) PCT Pub. No.: WO2013/170748
PCT Pub. Date: Nov. 21, 2013

(65) Prior Publication Data
US 2015/0352215 A1 Dec. 10, 2015

(30) Foreign Application Priority Data

May 15, 2012 (CN) .......................... 2012 1 0151073
May 15, 2012 (CN) .......................... 2012 1 0151464

(51) Int. Cl.
| | | |
|---|---|---|
| *C12N 15/82* | (2006.01) | |
| *C12N 15/113* | (2010.01) | |
| *A61K 31/713* | (2006.01) | |
| *A61K 31/7105* | (2006.01) | |
| *C12N 15/11* | (2006.01) | |

(52) U.S. Cl.
CPC ........ *C12N 15/8257* (2013.01); *A61K 31/713* (2013.01); *A61K 31/7105* (2013.01); *C12N 15/111* (2013.01); *C12N 15/113* (2013.01); *C12N 15/8218* (2013.01); *C12N 2310/14* (2013.01); *C12N 2310/141* (2013.01); *C12N 2320/30* (2013.01); *C12N 2320/32* (2013.01); *C12N 2330/50* (2013.01)

(58) Field of Classification Search
None
See application file for complete search history.

(56) References Cited

U.S. PATENT DOCUMENTS

| | | | | |
|---|---|---|---|---|
| 7,985,581 B2* | 7/2011 | Pachuk | ............... | C12N 15/1131 435/320.1 |
| 7,993,831 B2* | 8/2011 | Latham | ................ | C12Q 1/6809 435/6.12 |
| 8,309,530 B2* | 11/2012 | Szentirmai | ........... | A61K 31/713 514/44 A |
| 2005/0059005 A1* | 3/2005 | Tuschl | ................. | C12N 15/113 435/6.14 |
| 2010/0196396 A1* | 8/2010 | Szentirmai | ........... | A61K 31/713 514/1.1 |

FOREIGN PATENT DOCUMENTS

| | | | | | |
|---|---|---|---|---|---|
| WO | | 2010/118477 | | 10/2010 | |
| WO | WO 2011/0211171 | | * | 2/2011 | ........... A61K 31/713 |
| WO | WO 2011/091209 | | * | 7/2011 | ............. A01N 43/00 |

OTHER PUBLICATIONS

Cheon et al. Enhanced delivery of siRNA complexes by sonoporation in transgenic rice cell suspension cultures. (2009) J. Microbiol. Biotechnol.; vol. 19; pp. 781-786.*
Obembe et al. Advances in plant molecular farming. (2011) Biotechnology Advances; vol. 29; pp. 210-222.*
Leung et al. RNA interference: from gene silencing to gene-specific therapeutics. (2005) Pharmacology and Therapeutics; vol. 107; pp. 222-239.*
Daniell et al. Plant-made vaccine antigens and biopharmaceuticals. (2009) Trends in Plant Science; vol. 14; pp. 669-679.*
Zhang et al. Exogenous plant MIR168a specifically targets mammalian LDLRAP1: evidence of cross-kingdom regulation by microRNA. (2012) Cell Research; vol. 22; pp. 107-126.*
Goldstein et al. Biopharmaceuticals derived from genetically modified plants. (2004) Q. J. Med.; vol. 97; pp. 705-716 (Year: 2004).*
International Search Report for application No. PCT/CN2013/075642, dated Aug. 22, 2013 (6 pages).
Q. Ren et al., "Construction of Plant Expression Vector for Cholera Toxin B Subunit and Its Expression in Ginseng Cells," Chin J Biologicals, vol. 22, No. 7 (Jul. 2009), p. 663-666.
C. Wang et al., "Construction of Vector for Expression of Human Insulin in Plant Cells," Chin J Biologicals, vol. 19, No. 4 (Jul. 2006), p. 344-346.
L. Zhang et al., "Exogenous plant MIR168a specifically targets mammalian LDLRAP1: evidence of cross-kingdom regulation by microRNA," Cell Research (2012) vol. 22, p. 107-126.

* cited by examiner

*Primary Examiner* — Cathy Kingdon Worley
(74) *Attorney, Agent, or Firm* — Hamre, Schumann, Mueller & Larson, P.C.

(57) ABSTRACT

The invention relates to plants as functional microRNA and/or functional siRNA vehicles, the preparation methods and uses thereof. In particular, disclosed in the present invention are plants or edible portions or extracts thereof as functional microRNA and/or functional siRNA vehicles and uses thereof. Also disclosed is a method for carrying the functional microRNA and/or functional siRNA, comprising the step of orally administering the plants or edible portions or extracts thereof to a subject in need thereof, wherein the plants or edible portions thereof express and carry the functional microRNA and/or functional siRNA vehicles, and the extracts contain the functional microRNA and/or functional siRNA.

12 Claims, 3 Drawing Sheets
Specification includes a Sequence Listing.

SEQUENCE LISTING

```
<160> NUMBER OF SEQ ID NOS: 15

<210> SEQ ID NO 1
<211> LENGTH: 25
<212> TYPE: RNA
<213> ORGANISM: Artificial sequence
<220> FEATURE:
<223> OTHER INFORMATION: synthesized siRNA

<400> SEQUENCE: 1
gaacaaaugg cacuaguaaa cugag                                           25

<210> SEQ ID NO 2
<211> LENGTH: 44
<212> TYPE: DNA
<213> ORGANISM: Artificial sequence
<220> FEATURE:
<223> OTHER INFORMATION: synthesized primer

<400> SEQUENCE: 2
gagaacaaat ggcactagta aactgagtct ctcttttgta ttcc                      44

<210> SEQ ID NO 3
<211> LENGTH: 43
<212> TYPE: DNA
<213> ORGANISM: Artificial sequence
<220> FEATURE:
<223> OTHER INFORMATION: synthesized primer
```

```
<400> SEQUENCE: 3
actcagttta ctagtgccat ttgttctcaa agagaatcaa tga                43

<210> SEQ ID NO 4
<211> LENGTH: 43
<212> TYPE: DNA
<213> ORGANISM: Artificial sequence
<220> FEATURE:
<223> OTHER INFORMATION: synthesized primer

<400> SEQUENCE: 4
actaagttta ctagtgacat tgttatcac aggtcgtgat atg                 43

<210> SEQ ID NO 5
<211> LENGTH: 44
<212> TYPE: DNA
<213> ORGANISM: Artificial sequence
<220> FEATURE:
<223> OTHER INFORMATION: synthesized primer

<400> SEQUENCE: 5
gataacaaat gtcactagta aacttagtct acatatatat tcct               44

<210> SEQ ID NO 6
<211> LENGTH: 25
<212> TYPE: DNA
<213> ORGANISM: Artificial sequence
<220> FEATURE:
<223> OTHER INFORMATION: synthesized primer

<400> SEQUENCE: 6
ctgcaaggcg attaagttgg gtaac                                    25

<210> SEQ ID NO 7
<211> LENGTH: 28
<212> TYPE: DNA
<213> ORGANISM: Artificial sequence
<220> FEATURE:
<223> OTHER INFORMATION: synthesized primer

<400> SEQUENCE: 7
gcggataaca atttcacaca ggaaacag                                 28

<210> SEQ ID NO 8
<211> LENGTH: 49
<212> TYPE: DNA
<213> ORGANISM: Artificial sequence
<220> FEATURE:
<223> OTHER INFORMATION: synthesized primer

<400> SEQUENCE: 8
tcgtatccag tgcagggtcc gaggtattcg cactggatac gacctcagt          49

<210> SEQ ID NO 9
<211> LENGTH: 26
<212> TYPE: DNA
<213> ORGANISM: Artificial sequence
<220> FEATURE:
<223> OTHER INFORMATION: synthesized primer

<400> SEQUENCE: 9
ggcggcggaa caaatggcac tagtaa                                   26

<210> SEQ ID NO 10
<211> LENGTH: 16
```

```
<212> TYPE: DNA
<213> ORGANISM: Artificial sequence
<220> FEATURE:
<223> OTHER INFORMATION: synthesized primer

<400> SEQUENCE: 10
gtgcagggtc cgaggt                                               16

<210> SEQ ID NO 11
<211> LENGTH: 50
<212> TYPE: DNA
<213> ORGANISM: Artificial sequence
<220> FEATURE:
<223> OTHER INFORMATION: synthesized primer

<400> SEQUENCE: 11
gtcgtatcca gtgcagggtc cgaggtattc gcactggata cgacgtcccg          50

<210> SEQ ID NO 12
<211> LENGTH: 21
<212> TYPE: DNA
<213> ORGANISM: Artificial sequence
<220> FEATURE:
<223> OTHER INFORMATION: synthesized primer

<400> SEQUENCE: 12
tggtcgtcgc ttggtgcaga t                                         21

<210> SEQ ID NO 13
<211> LENGTH: 16
<212> TYPE: DNA
<213> ORGANISM: Artificial sequence
<220> FEATURE:
<223> OTHER INFORMATION: synthesized primer

<400> SEQUENCE: 13
gtgcagggtc cgaggt                                               16

<210> SEQ ID NO 14
<211> LENGTH: 22
<212> TYPE: RNA
<213> ORGANISM: homo sapiens

<400> SEQUENCE: 14
uggaguguga caauggguguu ug                                       22

<210> SEQ ID NO 15
<211> LENGTH: 25
<212> TYPE: DNA
<213> ORGANISM: Artificial sequence
<220> FEATURE:
<223> OTHER INFORMATION: synthesized nucleotides

<400> SEQUENCE: 15
gaacaaatgg cactagtaaa ctgag                                     25
```

PLANTS AS FUNCTIONAL MICRORNA AND/OR FUNCTIONAL SIRNA CARRIERS, PREPARATION METHODS AND USES THEREOF

TECHNICAL FIELD

The present invention relates to the biological field, particularly to plants as carriers of functional microRNA and/or functional small interfering ribonucleic acid (siRNA), and the preparation method and application of said carrier.

BACKGROUND ART

Small interfering ribonucleic acids (siRNA) are a type of double-strand RNA molecules composed of more than 20 nucleotides, which can exert an effect of silencing gene expression by specifically degrading the messenger ribonucleic acids (messenger RNA, mRNA) of target genes, and this process is called RNA interference (RNAi) and plays an important role in gene regulation and growth and development, etc. RNA interference (RNAi) is an antiviral mechanism. It is a sequence-specific posttranscriptional gene silencing of homologous genes mediated by dsRNA, and the effective mode of action thereof in cells is siRNA. RNA interference can utilize a siRNA or siRNA expression vector to specifically silence target genes, and this mode is rapid, cost-effective, simple and convenient, and has high sequence specificity, which can knock out the expression of target genes in a manner of acquiring loss of function or reducing the specificity of mutant sequence, and become an important research means for discovering gene functions. Progresses have been made in antiviral and tumor studies since RNAi can specifically down-regulate the expression and replication of particular genes. During the research on gene therapy with respect to HIV-1, hepatitis B, hepatitis C and the like using RNA interference technology, it has been discovered that selecting a sequence from a viral genome without homology to human genome as an inhibitory sequence can inhibit the viral replication while avoiding the toxic and adverse effects on normal tissues. Meanwhile, the inhibitory sequence which is selectively located at the particular site can produce apoptosis-inducing effects on partial malignant tumor cells which have definite gene mutation. In addition, siRNA expression directed to certain oncogenes or apoptosis molecules can yet be induced through using tumor-specific promoters, thereby achieving the purpose of specifically killing tumor cells.

Small interfering ribonucleic acids (siRNA) which can play a role in more specifically inhibiting target genes through artificial design of a siRNA sequence are widely used in gene regulation. Although RNA interference has been widely used in various aspects in biomedicine research, there are currently still some problems for this technology which are difficult to solve. Among them, the poor stability and low efficiency in delivering siRNA are the main reasons which hamper its application. Research have shown that the artificially synthesized siRNA which belongs to the small RNA family is generally rather unstable and liable to be degraded by the RNase in the circulatory system and becomes more intolerant to the acidic and basic environment in the digestive tract. For example, RNase belonging to the RNase A family in serum leads to the degradation of siRNAs (Haupenthal et al., Inhibition of RNase A family enzymes prevents degradation and loss of silencing activity of siRNAs in serum), therefore, the inhibition of RNase A in serum can prevent the weakness of degrading and silencing effects of siRNAs. The study also indicated that the degradation of siRNA is closely related to its sequence. Therefore, a variety of measures (including chemical modification, liposome encapsulation and the like) would be tried when applying siRNA in order to resist the degradation by the RNase.

Micro-ribonucleic acids (microRNA) are defined as a kind of evolutionarily conserved non-coding single-strand small ribonucleic acid molecules of approximately from 19 to 23 nucleotides in length. MicroRNA is capable of being completely paired with target mRNA, mediating the degradation of target mRNA or inhibiting the translation of proteins encoded by target mRNA, and regulating the gene expression at a posttranscriptional level as a regulator of gene expression. MicroRNA exists extensively within the genomes of animals and plants. Recent research finds that microRNA plays a very important role in the temporal regulation and the occurrence of diseases in organisms. MicroRNA is capable of controlling the growth, differentiation, and apoptosis of cells, and participating in many normal physiological activities, such as the individual development, tissue differentiation, apoptosis, and energy metabolism and the like in organisms; meanwhile, the expression of microRNA is related to cancers and plays an important role in the course of tumor formation. Approximately half of the upstream genes of microRNA are located at the tumor-related areas within chromosomes, which can play the role of oncogene and also can play the role of tumor suppressor gene during the occurrence and development of tumors. Plant microRNA likewise has no open reading frame (ORF) as animal microRNA and manifests evolutionary conservation and has higher complementarity with its target gene sequences. The binding sites of plant microRNA and target genes are not only limited to the 3' untranslated region (untranslated region, UTR) of the target genes, but also located at the transcribed region. Plant microRNAs are a kind of negative regulators for the gene expression of eukaryotes, which regulate the expression of plant gene mainly at a posttranscriptional level through medicating the cleavage of mRNA target molecules or reducing the translation of the target molecules, thereby regulating the morphogenesis of plant organs, growth and development, hormone secretion, and signal transduction, and the ability of response of the plants to the stress factors of the external environment.

Although microRNA has been widely used in biomedicine research, currently there exists some problems which are the main reasons that hamper its further development, for example, how to effectively deliver microRNA into animal body and allow it to function adequately in vivo. The effective contents of some microRNAs which have important functions on human and animals are relatively low in animals and plants, and it is very hard to reach a therapeutically effective amount per food intake by means of direct food intake.

Currently, the carriers for siRNA or microRNA are primarily liposomes, millimicrocapsules (Nanocapsules/Nanoparticles), -β cyclodextrin clathrate compound (β-cyclodextrin inclusion Compound) or β cyclodextrin capsules and the like; although the efficiency of delivering siRNA or microRNA is improved to some extent, the stability and efficiency are insufficient, and there is considerable toxicity.

Therefore, there is an urgent need for a more stable, efficient, and safe carrier for siRNA and/or microRNA and a method for delivering siRNA and/or microRNA.

CONTENTS OF THE INVENTION

One of the objects of the present invention is to provide a carrier for functional siRNA and/or functional microRNA, said carrier efficiently delivers functional siRNA and/or functional microRNA into an animal body and absorbed by the animal, thereby regulating the physiological activities of the animal without toxicity to the animal body and substantially having no side effect.

Another object of the present invention is to provide a method of efficiently delivering functional siRNA and/or functional microRNA.

In the first aspect, the present invention provides a carrier for functional siRNA, said carrier being selected from the group of:

(a) a plant or edible part thereof, and said plant or the edible part thereof expressing and carrying said functional siRNA; or (b) extracts of said plant, said extracts containing said functional siRNA.

In another one preferred example, said functional siRNA is non-naturally-occurring siRNA in said plant.

In another one preferred example, said functional siRNA (i) regulates the expression of the siRNA targeted gene in an animal, or (ii) ameliorates or treats siRNA targeted gene-related diseases.

In the second aspect, the present invention provides a carrier for functional microRNA, said carrier being selected from the group of:

(a) a plant or an edible part thereof, and said plant or the edible part thereof expressing and carrying said exogenous functional microRNA; or (b) extracts of said plant, said extracts containing said exogenous functional microRNA.

In another one preferred example, said functional microRNA is non-naturally-occurring microRNA in said plant.

In another one preferred example, said functional microRNA (i) regulates the expression of the target gene in an animal, or (ii) ameliorates or treats microRNA targeted gene-related diseases.

In another one preferred example, the plants described in the first aspect and the second aspect include: plants of Gramineae, typhaceae, Pteridiaceae, Compositae, Lamiaceae, Liliaceae, Amaryllidaceae, Boraginaceae, Araceae, Umbelliferae, Cruciferae, Primulaceae, Polygonaceae, Chenopodiaceae, Caryophyllaceae, Onagraceae, Urticaceae, Plantaginaceae, Myricaceae, Moraceae, Cannabaceae, Saxifragaceae, Rosaceae, Leguminosae, Pteridiaceae, Violaceae, *Lactuca seriola*, Amaranthaceae, Fagaceae, Chlorellaceae, Theaceae, Rubiaceae, Sterculiaceae, Pinaceae, Cucurbitaceae, Flacourtiaceae, Podocarpaceae, Betulaceae, Juglandaceae, Piperaceae, Magnoliaceae, Hydnaceae, Auriculariaceae, Tricholomataceae, Agaricaceae, Russulaceae, Ericaceae, Rosaceae, Actinidiaceae, Aizoaceae, Vitaceae, Annonaceae, Begoniaceae, Bromeliaceae, Capparaceae, Ginkgoaceae, Illiciaceae, Zingiberaceae, Punicaceae, Ranunculaceae, Apocynaceae, Berberidaceae, Rutaceae, Solanaceae, Papaveraceae, Verbenaceae, Pyrolaceae, Commelinaceae, Thymelaeaceae, Loranthaceae, Asclepiadaceae, Saururaceae, Crassulaceae, Lin-xiang family, Portulacaceae, Alismaceae, Malvaceae, Scrophulariaceae, Bignoniaceae, Menispermaceae, Schizaeaceae, Acanthaceae, Convolvulaceae, Polyporaceae, Sapindaceae, Cupressaceae, Simaroubaceae, Euphorbiaceae, Meliaceae, Combretaceae, Caprifoliaceae, Tamaricaceae, Orobanchaceae, Juncaceae, Hamamelidaceae, Gentianaceae, Tiliaceae, Acoraceae, Aquifoliaceae, Plantaginaceae, Anacardiaceae, Schisandraceae, Araliaceae, Bombacaceae, Aristolochiaceae, Oleaceae, Palmaceae, Nymphaeaceae, Santalaceae, or a combination thereof.

In another one preferred example, said plants are leaf lettuce, rice, wheat, corn, peanut, sorghum, soybean, potato, barley, goosefoot, thistle, pepper, anise, fennel, peach, apricot, pear, apple, banana, hedgehog hydnum, jew's ear, Chinese yam, hawthorn, ginseng, Chinese angelica, tomato, hot pepper, eggplant, carrot, cabbage, cauliflower, Chinese cabbage, pakchoi, rape, spinach, mustard, pea, pumpkin, cucumber, watermelon, melon, asparagus, onion, or a combination thereof.

In another one preferred example, said edible part includes: root, stem, leaf, flower, fruit, bud, seed, or a combination thereof.

In another one preferred example, said extracts are extracts of following edible parts: root, stem, leaf, flower, fruit, bud, seed, or a combination thereof.

In the third aspect, provided is the use of the carrier of the functional siRNA described in the first aspect of the present invention in the preparation of a composition carrying the functional siRNA.

In another one preferred example, said composition comprises a pharmaceutical composition, a food composition or a health care product.

In another one preferred example, said functional siRNA (i) regulates the expression of the target gene in an animal, or (ii) ameliorates or treats siRNA targeted gene-related diseases.

In another one preferred example, said siRNA targeted gene includes an animal gene and a gene of a pathogen (including bacteria, viruses, and chlamydia, etc.).

In another one preferred example, said diseases include tumors, acute and chronic infectious diseases or other acute and chronic diseases;

Among them, said acute and chronic infectious diseases include the diseases selected from the group of acute and chronic viral infectious diseases, acute and chronic bacterial infectious diseases and acute and chronic infectious diseases caused by pathogenic microorganisms;

Said other acute and chronic diseases include the diseases selected from the group of respiratory system diseases, immune system diseases, blood and hematopoietic system diseases, metabolic diseases related to endocrine system, digestive system diseases, nervous system diseases, urinary system diseases, reproductive system diseases and motor system diseases.

In another one preferred example, said acute and chronic viral infectious diseases include the diseases selected from the group of viral diseases including viral influenza, viral hepatitis, acquired immunodeficiency syndrome, SARS and the like; and said acute and chronic bacterial infectious diseases include the diseases selected from the group of tuberculosis and bacterial pneumonia.

In another one preferred example, said blood and hematopoietic system diseases include circulatory system diseases such as cardiovascular and cerebrovascular diseases.

In the fourth aspect, provided is the use of the carrier of the functional microRNA described in the second aspect of the present invention in the preparation of a composition carrying the functional microRNA.

In another one preferred example, said composition comprises a pharmaceutical composition, a food composition or a health care product.

In another one preferred example, said functional microRNA (i) regulates the expression of the microRNA targeted gene in an animal, or (ii) ameliorates or treats microRNA targeted gene-related diseases.

In another one preferred example, said microRNA targeted gene includes an animal gene and a gene of a pathogen (including bacteria, viruses, and chlamydia, etc.).

In another one preferred example, said diseases include tumors, acute and chronic infectious diseases or other acute and chronic diseases;

Among them, said acute and chronic infectious diseases include the diseases selected from the group of acute and chronic viral infectious diseases, acute and chronic bacterial infectious diseases and acute and chronic infectious diseases caused by pathogenic microorganisms;

Said other acute and chronic diseases include the diseases selected from the group of respiratory system diseases, immune system diseases, blood and hematopoietic system diseases, metabolic diseases related to endocrine system, digestive system diseases, nervous system diseases, urinary system diseases, reproductive system diseases and motor system diseases.

In another one preferred example, said acute and chronic viral infectious diseases include the diseases selected from the group of viral diseases including viral influenza, viral hepatitis, acquired immunodeficiency syndrome, SARS and the like; and said acute and chronic bacterial infectious diseases include the diseases selected from the group of tuberculosis and bacterial pneumonia.

In another one preferred example, said blood and hematopoietic system diseases include circulatory system diseases such as cardiovascular and cerebrovascular diseases.

In the fifth aspect, the present invention provides a method for carrying functional siRNA, which comprises the step of orally applying a plant or an edible part thereof or extracts thereof to a subject in need of treatment, in which said plant or the edible part thereof expresses and carries functional siRNA, and said extracts contain said functional siRNA.

In another one preferred example, also included is a step of expressing functional siRNA in the plant prior to said step.

In another one preferred example, said functional siRNA is non-naturally-occurring siRNA in said plant.

In another one preferred example, said functional siRNA (i) regulates the expression of the target gene in an animal, or (ii) ameliorates or treats siRNA targeted gene-related diseases.

In the sixth aspect, the present invention provides a method for carrying functional microRNA, which comprises the step of orally applying a plant or an edible part thereof or extracts thereof to a subject in need of treatment, in which said plant or the edible part thereof expresses and carries exogenous functional microRNA, and said extracts contain said exogenous functional microRNA.

In another one preferred example, also included is a step of expressing functional microRNA in the plant prior to said step.

In another one preferred example, said functional microRNA is non-naturally-occurring microRNA in said plant.

In another one preferred example, said microRNA (i) regulates the expression of the target gene in an animal, or (ii) ameliorates or treats microRNA targeted gene-related diseases.

In the seventh aspect, the present invention provides a method for regulating the expression of a target gene in an animal, said target gene is regulated by a functional siRNA, which method comprises orally applying a plant or an edible part thereof or extracts thereof to a subject in need of treatment, in which said plant or the edible part thereof expresses and carries functional siRNA, and said extracts contain said functional siRNA.

In another one preferred example, said method is also used for treating siRNA targeted gene-related diseases.

In another one preferred example, said diseases are the same as the diseases described in the third aspect of the present invention.

In the eighth aspect, the present invention provides a method for regulating the expression of a target gene in an animal, said target gene is regulated by a functional microRNA, which method comprises orally applying a plant or an edible part thereof or extracts thereof to a subject in need of treatment, in which said plant or the edible part thereof expresses and carries exogenous functional microRNA, and said extracts contain said exogenous functional microRNA.

In another one preferred example, said method is also used for treating microRNA targeted gene-related diseases.

In another one preferred example, said diseases are the same as the diseases described in the fourth aspect of the present invention.

In the ninth aspect, the present invention provides a method for improving the stability of functional siRNA, which comprises the step of introducing said functional siRNA or a vector expressing said functional siRNA into a plant, thereby allowing said plant or the edible part thereof to express said functional siRNA.

In another one preferred example, said method also comprises extracting or separating the expressed functional siRNA from said plant.

In the tenth aspect, the present invention provides a method for improving the stability of functional microRNA, which comprises the step of introducing said functional microRNA or a vector expressing said functional microRNA into a plant, thereby allowing said plant or the edible part thereof to express said functional microRNA.

In another one preferred example, said method also comprises extracting or separating the expressed functional microRNA from said plant.

In the eleventh aspect, the present invention provides a composition for ameliorating or treating a target gene-related disease in an animal, said target gene-related disease includes siRNA targeted gene-related diseases and/or microRNA targeted gene-related diseases, said composition comprises:

(1) a pharmaceutically acceptable carrier, an acceptable carrier in health products or an acceptable carrier in bromatology; and (2) (a) a plant or an edible part thereof, wherein said plant or the edible part thereof expresses and carries the functional siRNA for ameliorating or treating said siRNA targeted gene-related diseases or the exogenous functional microRNA for ameliorating or treating said microRNA targeted gene-related diseases; or (b) extracts of said plant, wherein said extracts contain said functional siRNA or exogenous functional microRNA.

In another one preferred example, said animal includes mammals such as human.

In another one preferred example, the composition of the present invention is an oral dosage form.

It should be understood that all of the various technical features described above and the various technical features specifically described hereinafter (such as examples) can be combined with one another within the scope of the present invention, so as to form new or preferred technical solutions. Due to space limitations, this is no longer tired out one by one.

PARTICULAR EMBODIMENTS

After conducting a long-term deep research, the inventors have unexpectedly found that with plant being used as a carrier for functional siRNA or exogenous functional microRNA, said functional siRNA or functional microRNA can not only substantially be expressed in plants, but also exist more stably, and can effectively enter an animal body through food intake. Experiments show that the functional siRNA or functional microRNA expressed by plants can not only tolerate the adverse environment of digestive tract and exist stably in an animal body, but also be more easily absorbed or enriched in an animal body (such as the circulatory system, tissues, and organs of the animal), thereby regulating (even silencing) target genes, thus facilitating the regulation of the physiological state of human body or treating siRNA or microRNA targeted gene-related diseases. The present invention is accomplished by the inventors on this basis.

As used herein, the term "siRNA targeted gene" always refers to a gene whose expression is interfered (particularly down-regulated) by said siRNA in an animal body.

As used herein, the term "microRNA targeted gene" always refers to a gene whose expression is interfered (particularly down-regulated) by said microRNA in an animal body.

As used herein, the term "target gene" includes a siRNA targeted gene and a microRNA targeted gene.

Said siRNA targeted gene or microRNA targeted gene can include an animal gene and a gene of a pathogen (including bacteria, viruses, and chlamydia, etc.).

siRNA Carrier of the Present Invention

As used herein, the terms "siRNA carrier", "functional siRNA carrier" or "functional siRNA plant carrier" can be used exchangeably and all of them refer to a carrier selected from the group of (a) a plant or an edible part thereof, wherein said plant or the edible part thereof expresses and carries said functional siRNA; or (b) extracts of said plant, wherein said extracts contain said functional siRNA.

Preparation Method of the siRNA Carrier of the Present Invention

The siRNA carrier of the present invention can be prepared using a conventional method in the art. In general, the method comprises introducing said siRNA or a vector expressing said siRNA into a plant (or part of plant cells), thereby allowing said plant or the edible part thereof to express said siRNA.

A preferred method for preparing siRNA plant carrier, which comprises the steps of:

1. construction of a vector which stably expresses the functional siRNA in a plant, which comprises the steps of providing a backbone vector suitable for siRNA expression; designing primers for particular siRNA sequences and obtaining the precursor sequence of siRNA using overlapping PCR amplification method; finally cloning the precursor sequence of siRNA into a binary expression vector; and identifying positive plasmids and transforming a strain of *Agrobacterium* for plant infestation;

2. construction of siRNA transformed plants, which comprises the steps of culturing sterilized seedlings, infesting with *Agrobacterium*, culturing plant calli for bud induction, and culturing seedlings for root induction;

3. detection and determination of siRNA in transformed plants, which comprises the preparation of RNA and cDNA, the detection of the expression of siRNA, and data processing.

4. detection of effects of transformed plants on the physiological and pathological states of animals, which comprises detecting the changes in the expression of corresponding target genes and the physiological and pathological indices.

siRNA

In general, siRNA is a double-strand RNA (dsRNA) of 21 nucleotides in length, in which the two strands have 2 nucleotides at respective two ends of RNA exceeding another end. The double-strand RNA (dsRNA) having homology can induce the sequence-specific silencing of the target gene through RNA interference (RNAi), which rapidly blocks gene activity. siRNA is an intermediate product in RNAi pathway and it is an essential factor for RNAi to exert effects. dsRNA would occur in cells under such circumstances as invasion of RNA virus and transcription of transposons and the like, and siRNA can be paired with the coding gene or UTR region of the target gene, thereby degrading the target gene.

The "siRNA" or "functional siRNA" described in the present invention refers to the non-naturally occurring siRNA in said plant (or plant carrier), especially the functional siRNA having beneficial effects on animal body (such as human), for example, said siRNA (i) regulates the expression of the target gene in an animal, or (ii) ameliorates or treats siRNA targeted gene-related diseases. The representative examples include the functional siRNA directed to an animal (especially human) gene and a pathogen gene, for example, including (but not limited to) HBV siRNA and the like.

In an preferred example, siRNA does not exist in said plant (or plant carrier) before said "siRNA" or "functional siRNA" being introduced into said plant (or plant carrier).

In another one preferred example, said "siRNA" or "functional siRNA" is artificially synthesized siRNA.

Application of the siRNA Carrier of the Present Invention

The siRNA carrier plants prepared by the present method have an extensive application prospect. The present invention uses a plant as the carrier for siRNA, which can specifically regulate the expression of target gene and can be used in drug development, nutritional diet and regulation of physiological and pathological states.

In particular, edible plant is selected and functional siRNA is substantially expressed in the plant, the functional siRNA can be delivered via the food intake pathway to achieve the purpose of gene silencing, thereby developing drugs, functional foods or heath care products. Alternatively, siRNA carrier plants which are constructed employing a synthetic siRNA and/or a vector expressing siRNA using the method recorded in the present invention or a conventional method known to a person skilled in the art enter human and animal bodies via the food intake pathway, and the functional siRNA can effectively inhibit the replication and expression of the target gene, thereby treating relevant diseases. For example, the functional siRNA can specifically inhibit the replication and expression of HBV and kill HBV virus, and thus can treat hepatitis B efficiently without toxic and side effects.

Composition Carrying siRNA

The carrier described in the present invention can be used for preparing a composition for carrying functional siRNA. Said composition can include a pharmaceutical composition, a food composition or a health care product.

The composition is further described taking a pharmaceutical composition as an example, and the pharmaceutical composition of the present invention can comprise:

(1) active ingredients: a safe and effective amount of a plant or an edible part thereof which expresses and carries functional siRNA; or extracts of said plant containing said functional siRNA, and (2) pharmaceutically acceptable excipients or carriers.

The "safe and effective amount" herein means that the amount of the active ingredient or said functional siRNA can obviously improve pathogenic conditions without producing severe side effect.

The examples of the pharmaceutically acceptable carrier include cellulose and derivatives thereof (such as sodium carboxymethylcellulose, sodium ethyl cellulose and the like), gelatin, talc, solid lubricant (such as stearic acid, magnesium stearate), calcium sulfate, a vegetable oil (such as soybean oil, sesame oil and the like), polyols (such as propylene glycol, glycerine and the like), an emulsifying agent (such as Tween®), a wetting agent (such as sodium lauryl sulfate), a colorant, a flavoring agent, a stabilizing agent, an antioxidant, a preservative and the like.

There is no special limitation to the application mode of the pharmaceutical composition and the representative application mode includes (but not limited to) oral administration.

Carrier for Functional MicroRNA of the Present Invention

As used herein, the terms "functional microRNA carrier" or "functional microRNA plant carrier" can be used exchangeably and all of them refer to a carrier selected from the group of (a) a plant or an edible part thereof, wherein said plant or the edible part thereof expresses and carries said exogenous functional microRNA; or (b) the extracts of said plant, wherein said extracts contain said exogenous functional microRNA.

Method for Preparing the Carrier for Functional MicroRNA of the Present Invention The functional microRNA plant carrier of the present invention can be prepared by a conventional method in the art or employing a method for preparing the siRNA carrier of the present invention with a difference that microRNA is used in place of siRNA.

Exogenous MicroRNA (Functional MicroRNA)

The "exogenous microRNA" described in the present invention refers to the non-naturally occurring microRNA in said plant (or plant carrier), especially the functional microRNA having beneficial effects on animal body (such as human), for example, said microRNA (i) regulates the expression of the target gene in an animal, or (ii) ameliorates or treats microRNA targeted gene-related diseases. The representative examples include functional microRNA derived from an animal (especially human), for example, including (but not limited to) hsa-miR-122-5p and the like.

Application of Plants as the MicroRNA Carriers

The microRNA carrier plants have extensive application prospects, and said functional microRNA carrier is applied in drug development, nutritional diet and regulation of physiological and pathological states and the like.

In particular, an edible plant is selected and functional microRNA of interest is substantially expressed in the plant, the functional microRNA of interest can be delivered via the food intake pathway to achieve the purpose of gene silencing, thereby developing pharmaceutical compositions, food compositions or heath care products. Alternatively, carrier plants carrying functional microRNA which are constructed employing a synthetic microRNA and/or a vector expressing microRNA using the method recorded in the present invention or a conventional method known to a person skilled in the art enter human and animal bodies via ingestion of the plant and exert regulating effects, for example, hsa-miR-122-5p which is carried into an animal body via this method can regulate the target genes in liver cancer cells both at cellular level and animal level, or make the liver cancer cells change the sensitivity to drugs through regulating the expression of the multiple drug resistance genes, and can thus treat liver cancer efficiently without toxic and side effects.

Composition Carrying MicroRNA

The carrier described in the present invention can be used for preparing a composition for carrying functional microRNA. Said composition can include a pharmaceutical composition, a food composition or a health care product.

The composition is further described taking a pharmaceutical composition as an example, and the pharmaceutical composition of the present invention can comprise:

(1) active ingredients: a safe and effective amount of a plant or an edible part thereof which expresses and carries exogenous functional microRNA; or extracts of said plant containing said exogenous functional microRNA, and (2) pharmaceutically acceptable excipients or carriers.

The "safe and effective amount" herein means that the amount of said active ingredient or said exogenous functional microRNA can obviously improve pathogenic conditions without producing severe side effect. The pharmaceutically acceptable carriers are as mentioned before.

There is no special limitation to the application mode of the pharmaceutical composition and the representative application mode includes (but not limited to) oral administration.

The main advantages of the present invention lie in that:

1. The plant or edible part thereof or extracts thereof are provided as siRNA carrier and uses thereof, said siRNA carrier can carry siRNA efficiently and stably into animal body and can be absorbed or enriched in an animal body (such as its circulatory system, tissues, and organs).

2. A method for more efficiently carrying siRNA is provided: the plant which expresses and carries functional siRNA is applied to an animal so as to carry said functional siRNA into animal body, so that functional siRNA is absorbed or enriched in an animal body (such as its circulatory system, tissues, and organs).

3. The plant or edible part thereof or extracts thereof are provided as microRNA carrier and uses thereof, said microRNA carrier can carry microRNA efficiently and stably into animal body and can be absorbed and enriched in an animal body (such as its circulatory system, tissues, and organs).

4. A method for more efficiently carrying microRNA is provided: the plant which expresses and carries exogenous functional microRNA is applied to an animal so as to carry said exogenous functional microRNA into an animal body, so that functional microRNA is absorbed or enriched in an animal body (such as its circulatory system, tissues, and organs).

The present invention is further illustrated in connection with particular embodiments as follows. It should be understood that these embodiments are merely illustrative of the invention and are not intended to limit the scope of the present invention. The experimental method where specific conditions are not specified in the following examples is generally performed in accordance with conventional conditions, such as the conditions described in Sambrook et al., *Molecular Cloning: A Laboratory Manual* (New York: Cold Spring Harbor Laboratory Press, 1989), or according to the conditions recommended by the manufacturer. All percentages and parts are calculated by weight unless otherwise indicated. The raw materials or instruments used in the examples of the present invention are all commercially available unless otherwise indicated.

Test Method

The methods used in the examples of the present invention are all common methods in the art, for example, include (but not limited to):

Method 1. Solexa sequencing technology, which comprises the particular steps of:

(1) collecting serum/plasma or tissue samples;

(2) extracting total RNA from serum with Trizol reagent;

(3) conducting PAGE electrophoresis to recover RNA molecules of 17-27nt;

(4) enzyme-linking adaptor primers to the 3' and 5' ends of small RNA molecules respectively;

(5) conducting cluster generation directly using purified DNA, and conducting sequencing analysis utilizing Illumina Genome Analyzer.

Method 2. Real-Time PCR Method

Real-time PCR method can be adopted as TaqMan method and fluorescent dye method.

2.1. TaqMan probe method, which comprises the following steps of:

(1) collecting serum, cell and tissue samples;

(2) extracting total RNA from serum with Trizol or Trizol LS reagent;

(3) reversely transcribing total RNA into cDNA using a siRNA probe or microRNA probe, AMV reverse transcriptase, and specific primers or stem-loop RT primers.

(4) conducting quantitative PCR using a PCR kit and Applied Biosystems 7300 fluorescence quantitative PCR instrument.

(5) conducting data processing method using $\Delta\Delta CT$ method, in which CT is set as cycle numbers when the reaction reaches the threshold value, a range of known concentrations of synthetic siRNAs or microRNAs are reversely transcribed and amplified, the absolute amounts of each siRNA or microRNA are drawn into a standard curve, and U6 snRNA is used as the standardized internal reference for cellular siRNA or microRNA expression. RNA is extracted from the serum samples from human and an animal, reverse transcription reaction is conducted, and the plant siRNA or microRNA amounts contained therein are compared by quantitative PCR reaction.

2.2. Real-time PCR experiment (fluorescent dye method) which comprises the following steps of:

(1) collecting serum, cell and tissue samples;

(2) extracting total RNA from serum with Trizol or Trizol LS reagent;

(3) reversely transcribing total RNA into cDNA using AMV reverse transcriptase and stem-loop RT primer.

(4) conducting quantitative PCR using a fluorescent dye EVA GREEN PCR kit and Applied Biosystems 7300 fluorescence quantitative PCR instrument.

(5) conducting data processing method using $\Delta\Delta CT$ method, in which CT was set as cycle numbers when the reaction reached the threshold value, a range of known concentrations of synthetic siRNAs or microRNAs were reversely transcribed and amplified, the absolute amounts of each siRNA or microRNA were drawn into a standard curve, and U6 snRNA was used as the standardized internal reference for cellular siRNA or microRNA expression. RNA was extracted from the serum samples from human and an animal, reverse transcription reaction was conducted, and the plant siRNA or microRNA contents in serum were compared by quantitative PCR reaction.

Example 1.1: Method for Constructing a Vector Plasmid Stably Expressing siRNA in Plants The sequence of the constructed vector is:

```
                                        (SEQ ID No.: 15)
          GAACAAATGGCACTAGTAAACTGAG;
```

The corresponding siRNA sequence after expression (5'→3') is:

```
                                        (SEQ ID NO.: 1)
          GAACAAAUGGCACUAGUAAACUGAG.
```

This siRNA is specifically directed to HBV virus, and is used for interfering with the genes for HBV expression and replication.

The primer sequences and names are as follows (5'→3', universal primers are shown in lowercase):

```
PZ6-P1:
                                        (SEQ ID NO.: 2)
gaGAACAAATGGCACTAGTAAACTGAGtctctcttttgtattcc PZ6-P2:
                                        (SEQ ID NO.: 3)
aCTCAGTTTACTAGTGCCATTTGTTCtcaaagagaatcaatga PZ6-P3:
                                        (SEQ ID NO.: 4)
aCTAAGTTTACTAGTGACATTTGTTAtcacaggtcgtgatatg PZ6-P4:
                                        (SEQ ID NO.: 5)
gaTAACAAATGTCACTAGTAAACTTAGtctacatatatattcct Primer A:
                                        (SEQ ID NO.: 6)
ctgcaaggcgattaagttgggtaac Primer B:
                                        (SEQ ID NO.: 7)
gcggataacaatttcacacaggaaacag
```

(1) Three pairs of primers as primer A and PZ6-P1, PZ6-P2 and PZ6-P3, and PZ6-P4 and primer B are used, the backbone vector (a strain deposited by State Key Laboratory of Pharmaceutical Biotechnology, School of Life Sciences, Nanjing University) is used as template (containing KpnI and BamHI cloning sites), and three fragments are obtained via PCR using primeSTAR High-Fidelity DNA Polymerase (Takara) with sizes of about 320 bp, 170 bp, 200 bp respectively, which are separated by 1.5% agarose gel electrophoresis and recovered by cutting the gel.

PCR reaction system (25 μL): 2×GC buffer 12.5 μL, dNTP (10 mM), primers (forward+reverse) 0.5+0.5 μL, template 1.0 μL, primeSTAR DNA polymerase 0.5 μL, dH$_2$O 9.0 μL.

PCR reaction conditions: 98° C. 5 min; 98° C. 10 s, 55° C. 5 s, 72° C. 30 s, for 35 cycles; 72° C. 7 min.

(2) the recovered three fragments are used as templates, primer A and primer B are used as primers, and full-length fragments with about 600 bp size required for PZ6 siRNA expression are obtained via overlapping PCR using primeSTAR High-Fidelity DNA Polymerase (Takara), then cloned into binary expression vector after being double-digested with Kpn I and BamHI, and sequenced to verify that whether mutation is introduced or not.

Overlapping PCR reaction system (25 μL) and the conditions thereof are as follows: 2×GC buffer 12.5 μL, dNTP (10 mM) 0.5 μL, primers (forward+reverse) 0.5+0.5 μL, templates 0.5+0.5+0.5 μL, primeSTAR DNA polymerase 0.5 μL, dH$_2$O 8.5 μL.

Overlapping PCR reaction conditions: 98° C. 5 min; 98° C. 10 s, 60° C. 5 s, 72° C. 40 s, for 35 cycles; 72° C. 7 min.

Expression vector ligation reaction system is: expression vector 3.0 μL, cleavage sites of BamHI and KpnI; T4 ligase (Takara) 2.0 μL, T4 ligase buffer 2.0 μL, H$_2$O 3.0 μL.

Ligation reaction conditions: ligating at 16° C. overnight.

(3) transformation of *Escherichia Coli*: *Escherichia Coli* are transformed using the conventional heat shock method. The correct plasmid is used for transforming a strain of *Agrobacterium*.

Extraction of *Agrobacterium* plasmid: the reagent used is domestic Karroten plasmid DNA extraction kit. The single clones are verified by sequencing, followed by shaking bacteria, and extracting plasmids according to the operating instructions of a kit.

Transformation of *Agrobacterium*: conventional electric shock method is employed. Finally, the successfully transformed *Agrobacterium* bacteria are identified and stored for transforming plants.

The construction of vector plasmid stably expressing siRNA is completed by the above-mentioned method.

Example 1.2: Construction of siRNA Transformed Plants

The experiments for siRNA transformed plants include culturing sterilized seedlings, infesting with *Agrobacterium*, culturing plant calli for bud induction, and culturing seedlings for root induction, which specifically comprise the following steps of:

The employed experiment for siRNA transformed plants herein is *Agrobacterium*-mediated method—leaf disc method. The surface of the plant seeds is sterilized with 10% NaClO for sterilization under shaking for about 10 min, followed by rinsing with sterile water for 4-5 times, air drying, inoculating onto a medium, and culturing at 25° C. for 5 d. The fresh leaf buds are sheared off, which are ready for subsequent plasmid transformation.

*Agrobacterium* bacteria carrying siRNA expression vector are cultured at 28° C. on a shaker up to OD600>1.0, followed by centrifuging to collect cells, and resuspending in 5% sucrose solution until OD600=1.0 to obtain a mixed liquid, that is, an infestation liquid.

Freshly sheared leaf buds of leaf lettuce are placed in the above-mentioned infestation liquid and cultured under suspension for 10 min, then placed onto a sterile filter paper so that surplus liquid can be absorbed, and the cotyledons are inoculated onto a ½ MS medium spread in advance with a layer of sterile filter paper. The leaf buds after which cultured for 2 d are rinsed with sterile water containing 4 mg/ml carbenicillin for 4-5 times and then inoculated to a bud induction medium. The ingredients for the bud induction medium comprise MS+2% sucrose+0.8% agar+0.01 mg/L NAA+0.1 mg/L 6-BA+200 mg/L carbenicillin+50 mg/L kanamycin.

The buds after being induced and sprouted are sheared off from explants and transferred to a root induction medium, radicle generation can be seen after about 7-10 d, and the ingredients for the root induction medium are as follows: ½ MS+0.01 mg/L NAA+30 mg/L kanamycin+50 mg/L carbenicillin+0.8% agar. The seedlings after taking roots are transferred to soil and cultured, and the expression of siRNA in plants is examined.

Among all the reagents used, MS salt is purchased from Duchefa Biochemie Company, and the rest reagents are products of Shanghai Sangon Biotech Co., Ltd.

Whether the construction of transformed plants succeeds is verified via example 1.3 after completing the construction.

Example 1.3: Experiment for Detecting siRNA in Transformed Plants

1. Preparation of RNA and cDNA.

Total RNA is extracted from plants after being transformed using Trizol reagent (Invitrogen Inc.). cDNA samples are prepared through conducting reverse transcription reaction on extracted RNA. The reaction system for reverse transcription comprise 2 μL 5×AMV buffer, 1 μL dNTP mixture (the concentration for each ingredient is 10 mM, Takara Inc.), 0.5 μL AMV (Takara Inc.), 2 μL RNA (1 μg/μL) and 0.5 μL siRNA-specific reverse primer mixture.

The total volume is 10 μL, and the reaction procedures are incubation at 16° C. for 30 min, reaction at 42° C. for 30 min, and incubation at 85° C. for 5 min.

2. Detection of siRNA Expression.

Two methods are employed for detection: semi-quantitative RT-PCR and real-time PCR 2.1 Semi-Quantitative RT-PCR The sequences of PZ6 reverse transcription primer and PCR primers are as follows:

PZ6 reverse transcription primer:
(SEQ ID NO.: 8)
TCGTATCCAGTGCAGGGTCCGAGGTATTCGCACTGGA TACGACCTCAGT;

PZ6 forward primer:
(SEQ ID NO.: 9)
GGCGGCGGAACAAATGGCACTAGTAA;

PZ6 reverse primer:
(SEQ ID NO.: 10)
GTGCAGGGTCCGAGGT.

MIR-168a reverse transcription primer and PCR primers are designed as follows:

MIR-168a-RT primer:
(SEQ ID NO.: 11)
GTCGTATCCAGTGCAGGGTCCGAGGTATTCGCACTGGATACGACGTCCCG;

MIR-168a forward primer:
(SEQ ID NO.: 12)
TGGTCGTCGCTTGGTGCAGAT;

MIR-168 a reverse primer:
(SEQ ID NO.: 13)
GTGCAGGGTCCGAGGT.

1 μL cDNA was taken, 0.3 μL Taq enzyme (Takara Inc.), PZ6 specific primer 0.5 μL each, 1.2 μL 25 mM $MgCl_2$, 0.4 μL dNTP mixture (the concentration for each ingredient is 2.5 mM, Takara Inc.), 2 μL 10×PCR buffer, and 14.1 μL $H_2O$ are added, and the system totally 20 μL is subjected to PCR.

The instrument used is ABI PCR Instrument, and the reaction conditions are 94° C. 5 min conducted for one cycle; 94° C. 15 second and 60° C. 1 min conducted for 40 cycles. MIR-168 is used as the internal reference. PCR products are subjected to 4% agarose gel electrophoresis for detection.

2.2 Real-Time PCR and Data Analysis.

1 μL cDNA is taken, 0.3 μL Taq enzyme (Takara Inc.), siRNA specific probe primer 0.33 μL, 1.2 μL 25 mM $MgCl_2$, 0.4 μL dNTP mixture (the concentration for each ingredient is 2.5 mM, Takara Inc.), 2 μL 10×PCR buffer, and 14.77 μL $H_2O$ are added, and the system totally 20 μL is subjected to PCR.

The instrument selected is ABI Prism 7300 fluorescence quantitative PCR instrument, and the reaction conditions are 95° C. 5 min conducted for one cycle; 95° C. 15 second and 60° C. 1 min conducted for 40 cycles. Three duplicate wells are conducted for each sample. Plant endogenous MIR-168 is used as the internal reference.

Relative comparison method which is also considered as ΔΔCt method is used for data processing. Ct is set as the number of cycles when the reaction reaches a threshold value, and $\Delta Ct = Ct_{sample} - Ct_{internal\ reference}$, in which the internal reference used is plant endogenous MIR-156. The expression amount of siRNA of each plant relative to wild-type control plants can be represented by an equation 2-ΔΔCT, in which $\Delta\Delta Ct = \Delta Ct_{sample} - \Delta Ct_{wild-type\ plant\ control}$, and the internal reference used is MIR-168. The experimental results show that the expression amount of siNRA in the plants after being transformed with siRNA is significantly higher than that of wild-type control group.

Figure 1:
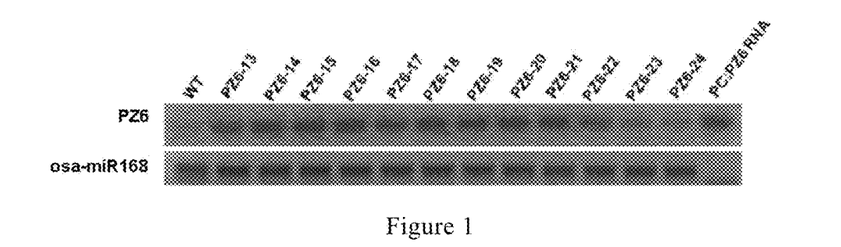
FIG. 1 shows the results of semi-quantitative RT-PCR for HBV siRNA in various transformed plants. PC is used as a positive control of synthetic RNA, and endogenous MIR-168 is used as a sample loading control. WT represents wild-type plants; PZ6-13, PZ6-14, PZ6-15, PZ6-16, PZ6-17, PZ6-18, PZ6-19, PZ6-20, PZ6-21, PZ6-22, PZ6-23, and PZ6-24 represent transformed plants; and PC: PZ6RNA is a positive control.
Figure 2:
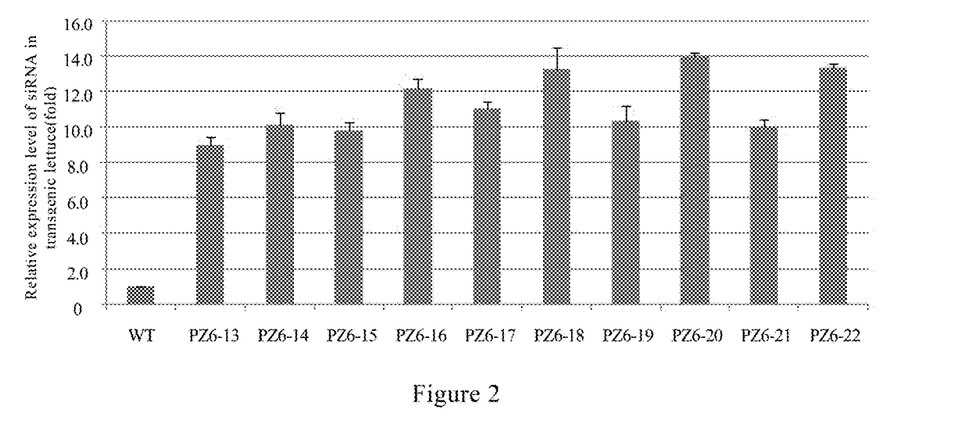
FIG. 2 shows the results of real-time PCR for HBV siRNA in various transformed plants. WT represents wild-type plants; PZ6-13, PZ6-14, PZ6-15, PZ6-16, PZ6-17, PZ6-18, PZ6-19, PZ6-20, PZ6-21, and PZ6-22 represent transformed plants.
Figure 3:
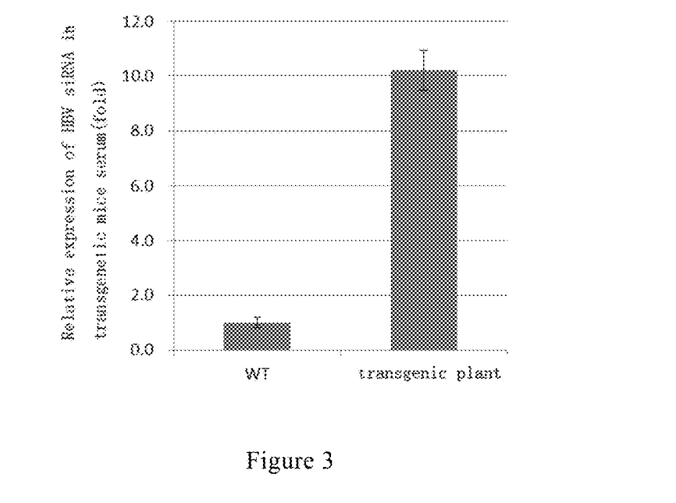
FIG. 3 shows the real-time PCR results for HBV siRNA in serum in transgenic mice after ingesting the transformed plants. WT represents the group of wild-type plants, and the transformed plants represent the group of transformed plants.
Figure 4:
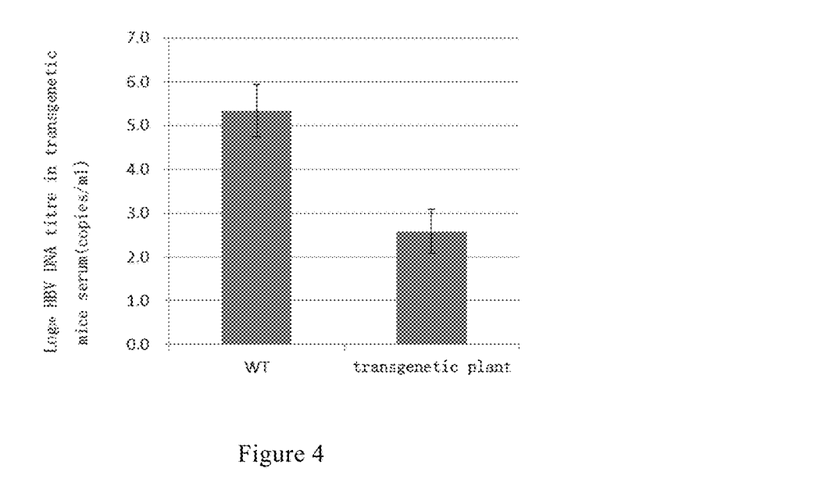
FIG. 4 shows the result of HBV DNA titer in serum in transgenic mice after ingesting the transformed plants. WT represents the group of wild-type plants, and the transformed plants represent the group of transformed plants.

The particular results are shown in FIG. 1 and FIG. 2.

FIG. 1 shows the results of semi-quantitative RT-PCR for HBV siRNA in various transformed plants. PC is used as a positive control of synthetic RNA, and endogenous MIR-168 is used as a sample loading control. WT represents wild-type plants; PZ6-13, PZ6-14, PZ6-15, PZ6-16, PZ6-17, PZ6-18, PZ6-19, PZ6-20, PZ6-21, PZ6-22, PZ6-23, and PZ6-24 represent transformed plants; and PC: PZ6RNA is positive control RNA.

The results show that the expression of HBV siRNA in transformed plants is increased as compared with wild-type (WT). The results indicate that the plants as siRNA carrier can substantially express siRNA in plants, allowing the expression of HBV siRNA increased.

FIG. 2 shows the results of real-time PCR for HBV siRNA in various transformed plants. WT represents wild-type plants; PZ6-13, PZ6-14, PZ6-15, PZ6-16, PZ6-17, PZ6-18, PZ6-19, PZ6-20, PZ6-21, and PZ6-22 represent transformed plants.

It can be seen from the results that the expression of HBV siRNA in transformed plants is significantly increased as compared with WT. It is indicated that siRNA can be expressed substantially in plants and the plants can be used as the siRNA carrier, thus achieving the purposes of effectively silencing the target gene and preparing drugs or functional foods.

Example 1.4: Changes in Physiological States of Animals After Ingesting the Transformed Plants This example demonstrates that siRNA enters the organs such as liver via the circulatory system of an animal after the transformed plants carrying siRNA expression vector are ingested by the animal, and regulates the physiological/pathological states of the animal.

Experimental method: firstly, transgenic mice of hepatitis B virus (HBV) are constructed for use in subsequent experimental research. The transgenic mice are hungry for 12 hours, then fed with transformed plants (constructed as the method described in example 1.2, identified via the method described in example 1.3 as significant expression increase of HBV siRNA in transformed plants), the changes in HBV siRNA and HBV-DNA in the serum of the transgenic mice are detected after feeding for 7 days; and the changes in five items of hepatitis B and the activity of glutamate pyruvate transaminase in the serum of the transgenic mice are detected after feeding for 30 days.

1.4.1 Preparation and Identification of Transgenic Mice Model of Hepatitis B Virus (HBV)

(1) Preparation of Gene Fragments for Microinjection:

The HBV whole genome is cloned to a backbone vector pBR322 plasmid (purchased from Promega Inc.) using molecular cloning method and amplified and purified;

(2) Microinjection and Transplantation of Fertilized Eggs:

Appropriate amount of DNA injection is inhaled using an injection needle under low power, and the fertilized eggs of mice are transferred into the droplets of M2 culture medium. The male pronucleus of fertilized egg is aimed by the tip of the injection needle under high power and rapidly pricked therein. The DNA liquid is injected slowly about 1 pl, the injection needle is rapidly withdrawn when the swelling of the male pronucleus can be seen. The individual egg cells are injected sequentially. The fertilized eggs after injection are immediately transferred into an M16 culture solution, and cultured in a CO$_2$ incubator for 30 min. The fertilized egg is transferred to an M2 culture solution from the M16 culture solution, and inhaled into an egg-transfer tube, the opening of the fallopian tube is found under an anatomical lens, and the fertilized egg is blown-in after inserting the egg-transfer tube into the fimbria of the fallopian tube. The incision is sutured after the operation is completed.

(3) The Detection of Integration of Transgenic Mice:

About 1 cm of mouse tail is sheared off 10-15 d after the birth of the mice and DNA is extracted. The DNA is amplified using HBV genome-specific primers, the amplified products are recovered using low melting point agarose gel electrophoresis, and then DNA sequencing analysis is conducted using a gene analyzer to verify whether the HBV gene is successfully transferred into the body of the mice. The sequencing results show that the HBV gene is integrated into genome.

(4) Detection of Hepatitis B Virus DNA (HBV-DNA) in Serum of Transgenic Mice:

The caudal artery of infant mouse of 1 month old is cut open, followed by taking blood, treating and collecting serum, centrifuging the serum at 2000× for 10 min, precipitating with PEG overnight, resuspending with lysis buffer (containing proteinase K 100 g/ml), incubating at 50° C. for 3 hours, and finally extracting with phenol and chloroform, and precipitating with ethanol to obtain serum HBV DNA. Serum HBV DNA level is detected using real-time PCR method, in which the real-time PCR method is described as test method 2.

(5) Detection of Hepatitis B Surface Antigen (HBSAg) in Serum of Transgenic Mice:

Infant mouse of 2 month old is taken and the caudal artery is cut open for taking blood and collecting serum according to the operation of (4). Hepatitis B surface antigen (HBSAg) level in serum of mice is detected using a conventional time-resolved fluoroimmunoassay.

The results show that HBV-DNA is detected in serum of constructed transgenic mice, and HBV secreted HBSAg in serum, which indicates that HBV transgenic mice model is constructed successfully. The HBV transgenic mice which are modeled successfully are selected for subsequent experiments.

1.4.2 In-Vivo Changes of Functional HBV siRNA in Transgenic Mice After Ingesting the Transformed Plants.

The expression level of HBV siRNA in serum after feeding transformed plants for 7 days is detected using real-time PCR. The particular procedures of real-time PCR experiment are as described in example 1.3. The particular results are shown in FIG. 3.

FIG. 3 shows that as compared with the mice which ingest wild-type plants (see WT in FIG. 3, the relative expression level of siRNA is set as 1), the expression of HBV siRNA in serum in transgenic mice after ingesting the transformed plants (see the transformed plants in FIG. 3) is significantly increased, the relative expression level of HBV siRNA is 10 folds of control group, which indicates that HBV siRNA in plants enters mice via the digestive system after ingestion and is enriched in the body of mice up to an extremely high effective concentration.

1.4.3 Changes in HBV-DNA in Serum in Transgenic Mice After Ingesting the Transformed Plants.

The expression level of HBV-DNA in serum after feeding the transformed plants for 7 days is detected using real-time PCR. The particular procedures of real-time PCR experiment are as described in example 1.3. The particular results are shown in FIG. 4.

FIG. 4 shows that as compared with ingestion of wild-type plants (see WT in FIG. 4, HBV DNA titer=105 copies/μl), the level of HBV-DNA (hepatitis B virus DNA) in serum in transgenic mice after ingesting the transformed plants (see the transformed plants in FIG. 4) is significantly reduced, the HBV DNA titer is reduced to about 1000 folds (102 copies/μl) of the original tiler, which indicates that HBV siRNA enters the body of transgenic mice after the transformed plants are ingested, thereby effectively inhibiting the proliferation and replication of hepatitis B virus, greatly reducing the number of hepatitis B viruses, and well exerting the effects of inhibiting the activity of hepatitis B virus.

1.4.4 Changes of Five Items of Hepatitis B in Serum in Transgenic Mice After Ingesting the Transformed Plants Five items of hepatitis B, also called as hepatitis B two-pair-half, include hepatitis B surface antigen (HBSAg), Hepatitis B surface antibody (anti-HBS), hepatitis B e antigen (HBeAg), hepatitis B e-antibody (anti-HBe), and hepatitis B core antibody (anti-HBc).

20 Transgenic mice are taken and divided into 2 groups, one group is fed with the transformed plants for 30 days; and the other group is fed with wild-type plants.

The levels of HBSAg, anti-HBS, HbsAb, anti-HBe, and anti-HBc in serum in transgenic mice of the two groups after feeding 30 days are detected using time-resolved fluoroimmunoassay. The particular procedures are as described in 1.4.1. The particular results see Table 1.

TABLE 1

| | before ingestion | | | | | after ingestion | | | | |
|---|---|---|---|---|---|---|---|---|---|---|
| ingestion plants | HBsAg | anti-HBS | HBeAg | anti-Hbe | anti-HBc | HBsAg | anti-HBS | HBeAg | anti-Hbe | anti-HBc |
| WT | + | − | + | − | + | + | − | + | − | + |
| | + | − | + | − | + | + | − | + | − | + |
| | + | − | + | − | + | + | − | + | − | + |
| | + | − | − | + | + | + | − | − | + | + |
| | + | − | − | + | + | + | − | − | + | + |
| | + | − | − | + | + | + | − | − | + | + |
| | + | − | − | − | + | + | − | − | − | + |
| | + | − | − | − | + | + | − | − | − | + |
| | + | − | − | − | + | + | − | − | − | + |
| | + | − | − | − | + | + | − | − | − | + |
| transgenic plants | + | − | + | − | + | − | − | − | + | − |
| | + | − | + | − | + | − | − | − | + | − |
| | + | − | + | − | + | − | − | − | − | − |

TABLE 1-continued

| ingestion plants | before ingestion | | | | | after ingestion | | | | |
|---|---|---|---|---|---|---|---|---|---|---|
| | HBsAg | anti-HBS | HBeAg | anti-Hbe | anti-HBc | HBsAg | anti-HBS | HBeAg | anti-Hbe | anti-HBc |
| | + | − | + | − | + | + | − | + | − | − |
| | + | − | + | − | + | + | − | − | − | − |
| | + | − | + | − | + | − | − | − | − | − |
| | + | − | − | − | + | − | − | − | − | + |
| | + | − | − | − | + | − | − | − | − | + |
| | + | − | − | + | + | − | − | − | − | + |
| | + | − | − | + | + | − | − | − | − | + |

− represents negative;
+ represents positive

The results show that among the transgenic mice after ingesting wild-type plants, the expression levels of HBSAg, anti-HBS, HbsAb, anti-HBe, and anti-HBc of 3 transgenic mice with "big three positive" (+-+-+), 3 transgenic mice with chronic HBsAg carriers (+--++), 4 transgenic mice with acute HBV infection (+----+) are not changed.

Among the 6 transgenic mice with "big three positive" (+-+-+) after the transgenic mice ingesting the transformed plants, 2 transgenic mice are turned to acute infection tended to recovery (---+-), 1 transgenic mouse is turned to "small three positive" (+---+-), 1 transgenic mouse is turned to an HBsAg carrier (+----), 2 transgenic mice substantially recover to the state of no infection of HBV (-----); 2 transgenic mice with acute HBV infection (+---+) are turned to an acute infection recovery period (----+); and 2 transgenic mice of chronic HBsAg carrier (+--++) are turned to an infection recovery period (----+) after ingesting the transformed plants.

The results of this example show that the conditions of all of the transgenic mice that ingested wild-type plants have no amelioration, whereas the transgenic mice after ingesting the transformed plants have different degrees of amelioration in liver function, for instance, the "big three positive" is turned to "small three positive", and the "big three positive" is turned to acute infection tended to recovery and the like. The research results show that siRNA in the plants can enter the body of mice together with the ingested transformed plants through feeding the mice with the transformed plants, achieve an effective concentration, and improve the pathological conditions of liver.

1.4.5 Determination of Activity of Glutamate Pyruvate Transaminase in Serum in Transgenic Mice After Ingesting the Transformed Plants The activity of glutamate pyruvate transaminase in serum 30 days after feeding the transformed plants is determined using spectrophotometry technology. The particular procedure comprises:

(1) collecting serum samples;
(2) drawing a standard curve;
(3) adding 0.5 ml of a glutamate pyruvate transaminase substrate solution to each test tube and blank tube, and incubating the tubes in 37° C. water bath for 5 min;
(4) adding 0.1 ml of serum to the test tube and mixing uniformly, followed by timing immediately, and further incubating in 37° C. water bath for 30 min;
(5) after 30 min, adding 0.5 ml of 2,4-dinitrophenylhydrazine solution to each test tube and blank tube, mixing uniformly, and supplementing 0.1 ml serum to the blank tube;
(6) adding 5 ml of 0.4 mol/L NaOH to each test tube and blank tube, followed by mixing uniformly, incubating 10 min, taking out, and cooling to room temperature;
(7) reading the determined absorbance A520 at 520 nm wavelength using the blank tube as the control;
(8) looking for the μmol of pyruvic acid on the standard curve and converting it into μg of pyruvic acid; and
(9) calculating the activity of glutamate pyruvate transaminase in serum.

Figure 5:
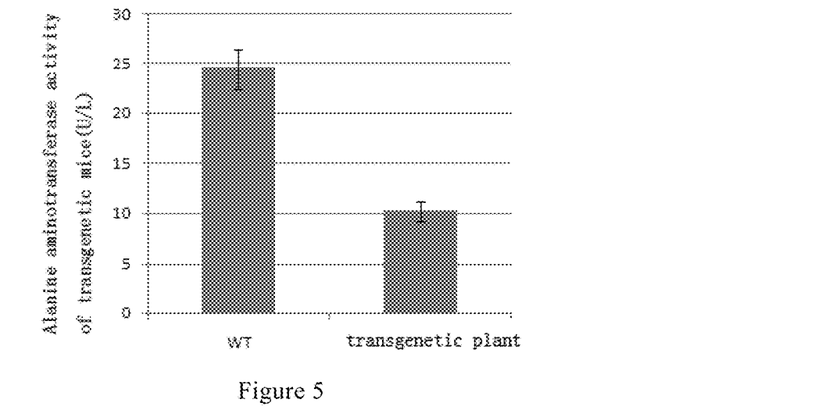
FIG. 5 shows the result of changes in the activity of glutamate pyruvate transaminase in serum in transgenic mice after ingesting the transformed plants. WT represents the group of wild-type plants, and the transformed plants represent the group of transformed plants.

The particular results are shown in FIG. 5. FIG. 5 shows that as compared with the ingestion of wild-type plants (see WT in FIG. 5), the activity of glutamate pyruvate transaminase in serum in transgenic mice after ingesting the transformed plants (see the transformed plants in FIG. 5) is significantly reduced by 58.3%.

The results indicate that the liver function of the mice is recovering gradually as the siRNA in the transformed plants exerts the effect of obviously killing the HBV viruses in the body of transgenic mice, and the transformed plants carrying siRNA can effectively reverse the liver injury of the mice and repair the liver function of the mice.

In summary, the results of this example show that plants can be used as the carriers of functional siRNA to effectively deliver functional siRNA to an animal body that ingests the plants and act on the target genes, thus regulating the physiological/pathological states.

Comparative Example 1.1 Low Stability of Artificially Synthesized HBV siRNA

The experimental method and test method are the same as example 1.4, with the difference that artificially synthesized HBV siRNA (its sequence is the same as shown in SEQ ID NO.: 1, with the difference that the sequence is obtained by fully artificial synthesis) would be fed.

The HBV siRNA is purchased from Invitrogen Inc., which is obtained via synthesis by Invitrogen Inc.

1 The results show that HBV siRNA is undetectable in serum or liver in the mice fed with artificially synthesized HBV siRNA.

2 The results find that as compared with the control group (without feeding artificially synthesized HBV siRNA), the HBV DNA level, the mRNA level in serum and hepatitis B surface antigen (HBSAg) in serum in the mice after ingesting artificially synthesized HBV siRNA had substantially no change.

It can be known in combination with example 1.4 that plants can be used as an exogenous siRNA carrier, can unexpectedly more effectively deliver exogenous siRNA into an animal body and act on corresponding target genes via delivery, thereby regulating the physiological activities of the animal.

Example 2.1: Method for Constructing a Vector Plasmid Stably Expressing Exogenous MicroRNA in Plants The sequence of the constructed vector is:

(SEQ ID No.: 15)
GAACAAATGGCACTAGTAAACTGAG;

The corresponding sequence of microRNA after expression (5'→3') is:

(SEQ ID NO.: 14)
UGGAGUGUGACAAUGGUGUUUG.

The microRNA is hsa-miR-122-5p used for interfering with NDRG1 gene.

The primers used in following experiments are designed according to the microRNA sequence to be expressed.

The particular procedure comprises:

(1) A backbone vector (strain deposited by State Key Laboratory of Pharmaceutical Biotechnology, School of Life Sciences, Nanjing University) is used as template, and three fragments are obtained via PCR reaction using primeSTAR High-Fidelity DNA Polymerase (Takara) with sizes of about 320 bp, 170 bp, 200 bp respectively, which are separated by 1.5% agarose gel electrophoresis and recovered by cutting the gel.

PCR reaction system (25 μL): 2×GC buffer 12.5 μL, dNTP (10 mM), primers (forward+reverse) 0.5+0.5 μL, template 1.0 μL, primeSTAR DNA polymerase 0.5 μL, dH₂O 9.0 μL.

PCR reaction conditions: 98° C. 5 min; 98° C. 10 s, 55° C. 5 s, 72° C. 30 s, for 35 cycles; 72° C. 7 min.

(2) the recovered three fragments are used as templates, and full-length fragments with about 600 bp size required for PZ6 microRNA expression are obtained via overlapping PCR reaction using primeSTAR High-Fidelity DNA Polymerase (Takara), then cloned into a binary expression vector after enzyme digestion, and sequenced to verify that whether mutation is introduced or not.

Overlapping PCR reaction system (25 μL): 2×GC buffer 12.5 μL, dNTP (10 mM) 0.5 μL, primers (forward+reverse) 0.5+0.5 μL, template 0.5+0.5+0.5 μL, primeSTAR DNA polymerase 0.5 μL, dH2O 8.5 μL.

Overlapping PCR reaction conditions: 98° C. 5 min; 98° C. 10 s, 60° C. 5 s, 72° C. 40 s, for 35 cycles; 72° C. 7 min.

Expression vector ligation reaction system is: expression vector 3.0 μL, cleavage sites of BamHI and KpnI; T4 ligase (Takara) 2.0 μL, T4 ligase buffer 2.0 μL, H₂O 3.0 μL.

Ligation reaction conditions for expression vector: ligating at 16° C. overnight.

(3) The transformation of *Escherichia Coli*, the extraction of plasmid of *Agrobacterium*, and the transformation of *Agrobacterium* are performed in accordance with that described in step (3) in example 1.1.

The construction of the vector plasmid stably expressing exogenous microRNA is completed by the above-mentioned method.

Example 2.2: Experiments for Exogenous MicroRNA Transformed Plants

The experiments for MicroRNA transformed plants include culturing sterilized seedlings, infesting with *Agrobacterium*, culturing plant calli for bud induction, and culturing seedlings for root induction.

The particular procedure is described as example 1.2, with the difference that using "*Agrobacterium* carrying an exogenous microRNA expression vector" in place of "*Agrobacterium* carrying a siRNA expression vector".

Whether the construction of transformed plants succeeds is verified via example 2.3 after completing the construction.

Example 2.3: Experiments for Detecting Exogenous MicroRNA in Transformed Plants This example employs a real-time PCR method to detect the expression amount of exogenous microRNA in the transformed plants.

The specific steps are as follows:

1. The preparation steps for RNA and cDNA are as step 1 in example 1.3, with the difference that the transformed plants obtained in example 2.2 are employed.

2. Real-time PCR method is employed to detect the expression amount of microRNA and data analysis is conducted.

1 μL cDNA is taken, 0.3 μL Taq enzyme (Takara Inc.), microRNA specific probe primer 0.33 μL, 1.2 μL 25 mM MgCl₂, 0.4 μL dNTP mixture (the concentration for each ingredient is 2.5 mM, Takara Inc.), 2 μL 10×PCR buffer, and 14.77 μL H₂O are added, and the system totally 20 μL is subjected to PCR.

The instrument selected is ABI Prism 7300 fluorescence quantitative PCR instrument, and the reaction conditions are 95° C. 5 min conducted for one cycle; 95° C. 15 second and 60° C. 1 min conducted for 40 cycles. Three duplicate wells are conducted for each sample.

Relative comparison method which is also considered as ΔΔCt method is used for data processing. Ct is set as the number of cycles when the reaction reaches a threshold value, and $\Delta Ct = Ct_{sample} - Ct_{internal\ reference}$. The expression amount of exogenous microRNA of each plant relative to wild-type control plants can be represented by an equation 2-ΔΔCT, in which $\Delta\Delta Ct = \Delta Ct_{sample} - \Delta Ct_{wild-type\ plant\ control}$. The experimental results show that the expression amount of exogenous microRNA in the plants after being transformed with exogenous microRNA is significantly higher than that of wild-type control group.

Figure 6:
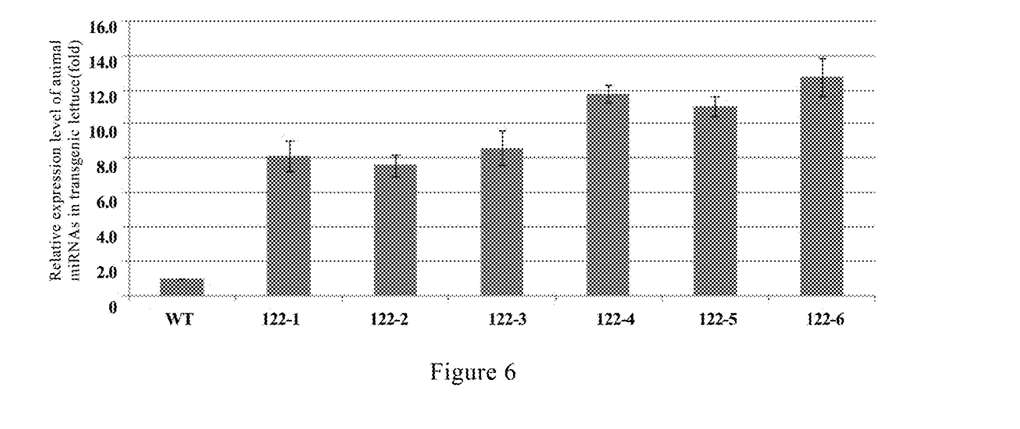
FIG. 6 shows the results of real-time PCR for human microRNA (hsa-miR-122-5p) in leaf lettuce. WT (Wild type) represents wild-type plants as a control; and 122-1, 122-2, 122-3, 122-4, 122-5, and 122-6 represent transformed plants.

The particular results are shown in FIG. 6. FIG. 6 shows the results of real-time PCR for human microRNA (hsa-miR-122-5p) in leaf lettuce. Wild-type represents wild-type plants as the control; and 122-1, 122-2, 122-3, 122-4, 122-5, and 122-6 represent transformed plants. It can be seen from the results that the expression of human microRNA in transformed plants is significantly increased as compared with the wild type.

The results show that exogenous functional microRNA can be delivered into plants and substantially expressed inside the plants.

Example 2.4: Changes in Physiological States of Animals After Ingesting the Transformed Plants This example demonstrates that siRNA enters the organs such as liver via the circulatory system of an animal after the transformed plants carrying microRNA (hsa-miR-122-5p) are ingested by the animal, and regulates the physiological and pathological states of the animal.

Experimental method: the liver cancer model mice are hungry for 12 hours, then fed with transformed plants carrying functional microRNA (hsa-miR-122-5p) constructed in example 2.2 for a period of time followed by detection.

2.4.1 Expression of Functional MicroRNA in an Animal After Ingesting the Transformed Plants The expression level of hsa-miR-122-5p in serum after feeding 7 days is detected using real-time PCR. The particular procedure for real-time PCR experiment is as described in test method 2.

The results show that the expression of hsa-miR-122-5p in serum and liver increases significantly, which indicates that hsa-miR-122-5p after ingestion enters the circulatory system and organs of mice and is enriched in vivo.

2.4.2 Expression of NDRG1 or Tumor State in an Animal After Ingesting the Transformed Plants Bioinformatics method is used to predict that hsa-miR-122-5p can regulate multiple target points including CAT-1 and NDRG1 (N-Myc downstream regulated gene 1) and the like. NDRG1 is a gene associated with differentiation, its expression in liver cancer tissue is significantly higher than paired paracancerous tissues, and the high expression of NDRG1 is associated with short-term survival rate, staging of advanced tumors, vascular invasion, large tumor volume, and high Edmondson-Steiner tissue grading. Immunohistochemistry is employed to discover that NDRG1 is significantly over-expressed in liver cancer tissue as compared with paracancerous liver tissue, liver cirrhosis tissue and benign liver lesion tissue, which indicates that the over-expression of NDRG1 is closely related to the degrees of differentiation of tumors and survival rate. The regulation of NDRG1 allows the NDRG1 to recover to a normal expression level, which is likely a new target point for the treatment of liver cancer.

Real-time PCR is employed after feeding 7 days to detect the expression level of NDRG1 gene in liver, and the particular procedure for real-time PCR experiment is as described in test method 2.

The results show that the expression of NDRG1 level is significantly decreased as compared with the control group (without feeding transformed plants carrying functional microRNA (hsa-miR-122-5p) constructed in example 2.2).

2.4.3 The liver cancer model mice after feeding 30 days is ameliorated to some extent, the detection of the size of tumor mass finds that as compared with the control group (without ingesting the transformed plants carrying the functional microRNA (hsa-miR-122-5p) constructed in example 2.2), the volume of liver tumor of the mice in experimental group becomes smaller significantly, the tumor weight is decreased significantly, and the tumor growth is inhibited.

Therefore, plants can be used as the carrier for hsa-miR-122-5p, unexpectedly more effectively deliver hsa-miR-122-5p to target gene, thus inhibiting the tumor growth through inhibiting corresponding target genes, and allowing tumor volume to significantly become smaller and tumor weight to become lighter.

In summary, plants as the carrier of functional microRNA express said functional microRNA substantially in the plants, and said functional microRNA is stably and effectively delivered into animal body via the pathway of ingestion and absorbed in an animal body, thereby effectively regulating the target gene in an animal body.

Comparative Example 2.1 Low Stability of Artificially Synthesized MicroRNA (hsa-miR-122-5p)

The experimental method and test method are the same as example 2.4, with the difference that artificially synthesized hsa-miR-122-5p (its sequence is the same as shown in SEQ ID NO.: 14, with the difference in that it is fully artificially synthesized) would be fed.

The artificial hsa-miR-122-5p is purchased from Takara Inc., which is obtained via synthesis by Takara Inc.

The results show that:

1 As compared with the control group (without feeding artificially synthesized hsa-miR-122-5p) with respect to serum hsa-miR-122-5p, the serum hsa-miR-122-5p content in the experimental group is not elevated and has no significant difference, that is to say, the artificially synthesized hsa-miR-122-5p is undetectable in serum, possibly because that the synthetic hsa-miR-122-5p is degraded since it is not modified.

2 As compared with the control group (without feeding artificially synthesized hsa-miR-122-5p), the expression of NDRG1 in the experimental group has no significant difference.

3 As compared with the control group (without feeding artificially synthesized hsa-miR-122-5p), the cancer model mouse tumor volume in the experimental group is not changed, the tumor weight is not changed, and there is no significant difference.

It can be seen in combination with example 2.4 that the artificially synthesized microRNA (hsa-miR-122-5p) cannot be stably delivered to body via the pathway of ingestion. However, the microRNA carrier of the present invention can be employed to effectively stably deliver said exogenous functional microRNA into an animal body, and the exogenous functional microRNA can stably exist in the animal serum.

Comparative Example 2.2 Preferential Absorption or Enrichment of Functional MicroRNA After Ingesting the Transformed Plants This example demonstrates that the transformed plants carrying functional microRNA (such as hsa-miR-122-5p) are preferentially absorbed or enriched after being ingested by the animal. The experimental method or detection method is the same as in example 2.4.

1. Expression of Plant MicroRNAs in Leaf Lettuce

Real-time PCR is employed to detect the expression level of plant microRNA MIR156a in leaf lettuce.

The result shows that plant microRNA MIR156a is expressed in leaf lettuce.

2. Expression of Plant MicroRNAs in an Animal Body After Ingesting Leaf Lettuce

Real-time PCR is employed to detect the expression level of plant microRNA MIR156a in serum and liver after ingesting leaf lettuce.

The results show that: The expression of plant microRNA MIR156a is increased to some extent as compared with the control group (without feeding the leaf lettuce).

3. The Tumors of Liver Cancer Model Mice After Feeding Leaf Lettuce are not Ameliorated, and the Size of Tumor Mass is Detected, The results find that as compared with the control group (without feeding the leaf lettuce), the liver tumor volume and the tumor weight of the mice in the experimental group have no significant change, and the tumor growth is not affected.

The results show that as compared with 2.4.1 in example 2.4, although the expression of the microRNA of the plant per se in serum and liver is increased to some extent, it is far less than the increase amount of the expression of hsa-miR- 122-5p. This indicates that the exogenous functional microRNA is absorbed preferentially.

Comparative Example 2.3 Instability of Synthetic Precursors of MicroRNAs in an Animal Body In order to detect the stability of artificially synthesized precursor (such as pre-MIR168a or pre-MIR156a) of plant microRNAs in an animal body, the following experiments are conducted:

1. RT-PCR is used to detect the stability of artificially synthesized precursor of plant microRNA in an animal body.

The liver cancer model mice are fed pre-MIR168a or pre-MIR156a, and the expression levels of pre-MIR168a or pre-MIR156a in various organs, feedstuffs, or rice are studied 6 hours after feeding different foods.

The specific steps are as follows:
(1) collecting serum, organ, feedstuff, and rice samples;
(2) extracting total RNA of the samples with Trizol or Trizol LS reagent;
(3) reversely transcribing total RNA into cDNA using AMV reverse transcriptase, the RT primers, and RNase inhibitor;
(4) conducting agarose gel electrophoresis of PCR products; and
(5) observing the results under an ultraviolet lamp after EB staining.

Figure 7:
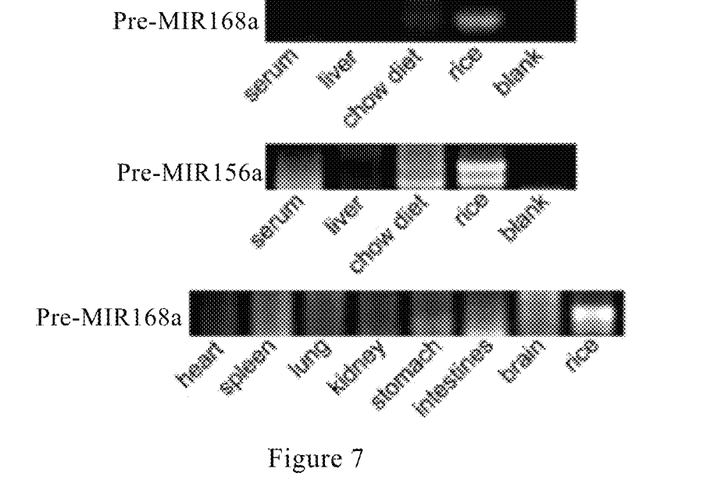
FIG. 7 shows the results of RT-PCR for the precursor of artificially synthesized plant microRNAs in various organs, feedstuffs or rice. The blank is used as a negative control, rice is used as a positive control, and the detected organs include heart, spleen, lung, kidney, stomach, intestine, and brain.

The particular results are shown in FIG. 7. FIG. 7 is the results of RT-PCR for the precursor of artificially synthesized plant microRNAs in various organs, feedstuffs or rice. Sanger method is employed to accurately amplify the artificially synthesized pre-MIR168a and pre-MIR156a. In the figure, the blank is used as the negative control, rice is used as the positive control, and it can be seen from the results that the synthesized pre-MIR168a is undetectable in serum, liver, and feedstuff as compared with the positive control. The synthesized pre-MIR156a is also undetectable in serum, liver, and feedstuff. The synthesized pre-MIR168a is undetectable in heart, spleen, lung, kidney, stomach, intestine, and brain. The results show that the synthetic precursors of microRNAs are not stable in an animal body.

2. Real time PCR method is employed to further detect the stability of the synthetic precursors of plant microRNAs in an animal body.

The liver cancer model mice are fed pre-MIR168a, and the expression levels of pre-MIR168a in serum are studied 6 hours after feeding different foods.

The expression level of pre-MIR168a in serum is detected using real-time PCR. The test method is as described in test method 2.

Figure 8:
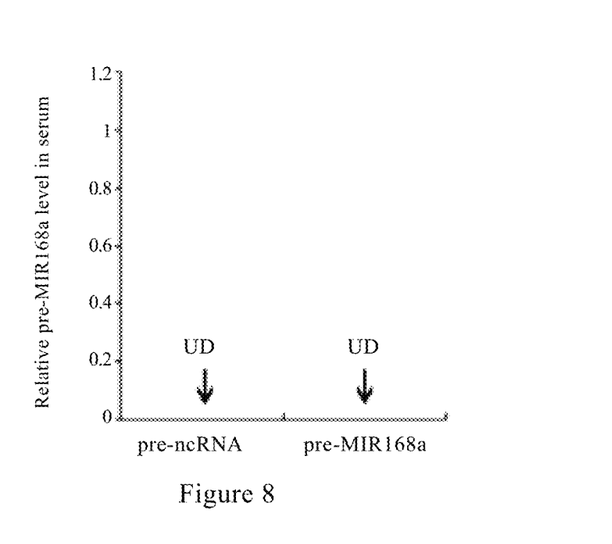
FIG. 8 shows the result of real-time PCR for the expression amount of precursor of the artificially synthesized plant microRNAs in animal serum. UD represents undetected.

The particular results are shown in FIG. 8. UD represents undetected. It can be seen from the results that as compared with the control group (ncRNA precursor (pre-ncRNA), pre-ncRNA is not stable in an animal body and therefore pre-ncRNA is undetectable in an animal serum), pre-MIR168a is undetectable in serum, which indicates that pre-MIR168a is not stable in serum and also cannot exert a regulatory effect.

In summary, artificially synthesized precursors of plant microRNAs cannot generally exist stably in animal serum and also cannot effectively perform their functions.

All the documents referred to in the present invention are incorporated by reference as if each reference cited as alone as a reference in the present application. In addition, it should be understood that after reading the teachings of the present invention described above, a skilled person in the art can make various changes or modifications of the invention, and these equivalent forms also fall into the scope as defined by the appended claims of the present application.

The invention claimed is:

1. A carrier for delivering exogenous functional microRNA comprising at least one product selected from the group consisting of:
   (a) a plant or an edible part thereof, said plant or edible part thereof expressing and carrying said exogenous functional microRNA; and
   (b) an extract of said plant or edible part thereof, said extract containing said exogenous functional microRNA, wherein said exogenous functional microRNA consists of SEQ ID NO:14;

said plant is leaf lettuce;

said exogenous functional microRNA regulates expression of a microRNA targeted gene, and said carrier carrying said exogenous functional microRNA ameliorates or treats a microRNA targeted gene-related disease in an animal; and said gene-related disease is a viral infectious disease or cancer.

2. The carrier of claim 1, wherein said edible part is selected from root, stem, leaf, flower, fruit, bud, and seed.

3. A method for preparing a composition for delivering exogenous functional microRNA into an animal body, comprising:
  i) introducing an exogenous functional microRNA or a vector expressing said exogenous functional microRNA into a plant;
  ii) obtaining a carrier
  wherein said carrier includes at least one product selected from the group consisting of:
    (a) said plant or an edible part thereof, said plant or edible part thereof expressing and carrying said exogenous functional microRNA, and
    (b) an extract of said plant or edible part thereof, said extract containing said exogenous functional microRNA,
    wherein said exogenous functional microRNA consists of SEQ ID NO:14,
      said plant is leaf lettuce,
      said exogenous functional microRNA regulates expression of a microRNA targeted gene, and said carrier carrying said exogenous functional microRNA ameliorates or treats a microRNA targeted gene-related disease in an animal, and
      said gene-related disease is a viral infectious disease or cancer.

4. The method of claim 3, wherein said microRNA targeted gene includes an animal gene or a gene of a pathogen including bacteria, viruses, chlamydia.

5. The method of claim 3, wherein said viral infectious disease includes an acute or chronic viral infectious disease.

6. A composition for ameliorating or treating a target gene-related disease in an animal, comprising:
  (1) a pharmaceutically acceptable carrier, an acceptable carrier in health products, or an acceptable carrier in bromatology; and
  (2) the carrier of claim 1.

7. A method for ameliorating or treating a microRNA target gene-related disease, comprising administering a composition including a carrier,
  wherein said carrier includes at least one product selected from the group consisting of:
    (a) a plant or an edible part thereof, said plant or edible part thereof expressing and carrying said exogenous functional microRNA, and
    (b) an extract of said plant or edible part thereof, said extract containing said exogenous functional microRNA,
    wherein said exogenous functional microRNA consists of SEQ ID NO:14,
      said plant is leaf lettuce,
      said exogenous functional microRNA regulates expression of a microRNA targeted gene, and said carrier carrying said exogenous functional microRNA ameliorates or treats a microRNA targeted gene-related disease in an animal, and
      said gene-related disease is a viral infectious disease or cancer.

8. The method of claim 7, said microRNA targeted gene includes an animal gene or a gene of a pathogen including bacteria, viruses, and *chlamydia*.

9. The method of claim 7, wherein said viral infectious disease includes an acute or chronic infectious disease.

10. The carrier of claim 1, wherein said carrier is an edible carrier and delivers said exogenous functional miRNA in the animal via food intake pathway.

11. The method of claim 7, wherein said composition is administered via food intake pathway.

12. The method of claim 7, wherein said composition is a pharmaceutical composition, a food composition or a health care product.

* * * * *